United States Patent [19]
Stöcker

[11] 4,339,241
[45] Jul. 13, 1982

[54] APPARATUS AND METHOD FOR SIMULTANEOUSLY MIXING SPECIMENS FOR PERFORMING MICROANALYSES

[76] Inventor: Winfried A. Stöcker, Krummesserweg 3, 2419 Rondeshagen, Fed. Rep. of Germany

[21] Appl. No.: 197,177

[22] Filed: Oct. 15, 1980

[30] Foreign Application Priority Data

Oct. 16, 1979 [EP] European Pat. Off. ........ 79103987.8

[51] Int. Cl.³ .................... G01N 33/50; G01N 33/54; G01N 33/80; B01F 11/00
[52] U.S. Cl. .................... 23/230 B; 23/230.3; 23/915; 23/920; 366/273; 366/287; 422/68; 424/1; 424/8; 424/11; 424/12; 435/7
[58] Field of Search .................. 422/68; 366/127, 273, 366/332, 333; 424/11; 23/230 B

[56] References Cited

U.S. PATENT DOCUMENTS

| | | | |
|---|---|---|---|
| 2,615,692 | 10/1952 | Muller | 366/273 |
| 3,680,843 | 8/1972 | Lu | 366/273 |
| 3,830,099 | 8/1974 | Ichikawa | 366/127 X |
| 3,873,268 | 3/1975 | McKie | 422/68 X |
| 4,056,359 | 11/1977 | Janin | 422/68 X |

*Primary Examiner*—Sidney Marantz
*Attorney, Agent, or Firm*—John T. Synnestvedt; Richard D. Weber

[57] ABSTRACT

An analysis system with which a random number of small to very small liquid specimens can be simultaneously examined side by side without hollow reaction vessels. The specimens do not mix together and do not dry out.

To this end, the plates are provided with a water-repelling coating leaving free a number of circular surfaces. The individual specimens are placed between the coinciding circular surfaces of two superimposed plates. A frame ensures that there can be no reciprocal lateral sliding of the plates and that the latter do not move too close to one another. For mixing of the individual specimens, the plates can be rhythmically moved towards and away from one another within given intervals, e.g. by means of a spring-magnet system.

The analysis system can be used in many immunological examinations, particularly blood group determinations, radioimmunoassays, enzyme-immunoassays, immunofluoroescent assays and in non-immunological, general chemical, biochemical and clinical chemical examinations.

17 Claims, 5 Drawing Figures

APPARATUS AND METHOD FOR SIMULTANEOUSLY MIXING SPECIMENS FOR PERFORMING MICROANALYSES

APPARATUS FOR PERFORMING MICROANALYSES

The invention relates to an apparatus for performing microanalyses and its use in immunological examinations, particularly blood group determinations, radioimmunoassays, enzyme-immunoassays, immunofluorescent assays and in non-immunological general chemical, biochemical and clinical-chemical investigations.

BACKGROUND OF THE INVENTION

The increasing demand for clinical-chemical and immunological analyses has led to the progressive miniaturization of research and investigation processes. As a result, labour time, space, material and reagents are saved. Most analyses are performed with vessels which limit the reaction mixture in five directions, namely to four sides and to the bottom. The space and material requirements could be further reduced by a support bounding the reaction mixture in only one or two directions. For example, in the case of blood group determinations, the reactions can take place on slides, this also applying to immunofluorescent assays on frozen sections (cf H. P. Seelig, H. P. Geisen and R. Seelig in Lab. med. 2, 1978, pp. 133–139). If, outside the reaction fields, the slides are covered with an inert, water-repellent layer, the various specimens which are on the slide at the same time cannot mix together as easily (cf P. O'Neill and G. D. Johnson in Ann. N.Y. Acad. Sci. 177, 1971, pp. 446–452; coating with polytetrafluoroethylene). In this process, the drops easily dry on the surface, even if the slides are in a moist chamber. This leads to spoiling or to a falsification of the analysis through the concentration of the dissolved substances rising. Thus, the technique recommended by Tung is frequently used (cf K. S. K. Tung in J. Immunol, Methods 18, 1977, pp. 391–392). According to this technique, a further uncoated slide is placed with a gap over the first slide in such a way that it is in contact with the underlying drops. However, the various specimens then often run together and mix. The specimens particularly tend to mix if a condensation water film has formed on the upper slide or if the two slides have not been accurately superimposed or if the upper slide with respect to the other, as well as when the drops have not been accurately positioned. The drops must therefore be kept a considerable distance from one another to prevent their running together. This is contrary to a reduction in size of the analytical apparatus. In addition, in this form, it is very difficult to automate the process. The reactions also last a relatively long time, because mixing within the drops must take place manually and individually in succession. For this purpose, a stirring rod is required for each drop, because mixing by tilting the slide is not very effective.

Austrian Pat. No. 170,898 (Inventor: Dr. F. Mandula) published on Apr. 10th, 1951 already discloses an apparatus for serological research in which a plurality of cup-shaped depressions are provided in a base plate. These depressions are filled with the substance under investigation. The depressions are then covered with a thin plate. The covered plate is placed in a vibrating apparatus where the substances placed in the cup-shaped depression are mixed by the vibrating movements.

DE-OS No. 2,527,770 (Inventors: Berndt and Timmermann), published on Jan. 13th, 1977 discloses a slide for performing agglutination reactions having a support plate with reaction fields arranged in grating or grid-like manner. The reaction fields are formed by individual mirrors, preferably having a planar reaction surface, whilst between the reaction fields, the area surrounding the mirrors is opaque or transparent and is also glare-free.

East German Pat. No. 96,784 (Inventors: Thielmann and Horn), published on Aug. 5th, 1976 discloses a process and an apparatus for measuring enzyme activities and substrate or cosubstrate concentrations in the ultramicro-range in which two superimposable plates made from a hard material, preferably plastic, are provided with chambers, preferably in the form of countersinks, surrounded by annular recesses which form reaction chambers on superimposing and clamping together the plates.

U.S. Pat. No. 3,783,105 (Moyer et al), patented on Jan. 1st, 1974 discloses an apparatus and a process for the quantified indication of the activities on a large number of enzymes present in biological fluids. For this purpose, microporous membranes are used as filters.

Finally, East German Pat. No. 107,783 (Inventor: Horn et al), published on Aug. 12th, 1974 discloses a specimen carrier for performing chemical analyses in the ultramicro range comprising two substantially planar plates which, at least on their facing surfaces have interengaging depressions and/or projections.

The object of the invention is to provide an analytical apparatus requiring only two limiting surfaces for each analysis.

Another object of the invention is to provide apparatus which permits examination of a large number of specimens simultaneously, while taking up the minimum amount of space and while preventing the specimens from mixing together. This leads to savings in labour time, material and reagents.

Another object of the invention is to provide apparatus which keeps the reaction times short for the rapid performance of the process.

A further object of the invention is to provide apparatus which can also be used outside a damp chamber.

Yet another object of the invention is to provide apparatus which is automated to the greatest possible extent while maintaining its suitability for use in many branches of biochemistry and clinical chemistry.

SUMMARY OF THE INVENTION

In the present invention, each of two glass or plastic plates of the same size are coated on one surface with a water-repellent substance in such a way that a given number of circular surfaces remain free. One of the two plates is placed horizontally in a base frame with the coated side upwards and consequently forms a so-called lower plate. A defined volume of an aqueous solution, usually a small drop, is placed on each circular surface of the lower plate.

The other plate, called the upper plate, is placed over the lower plate with the coated side downwards. The circular surfaces of both plates are congruently juxtaposed. Both plates are in contact with the intermediate drops of solution. The base frame is constructed in such a way that the upper and lower plates cannot be horizontally displaced with respect to one another and maintain a clearly defined minimum reciprocal spacing. The drops between the circular surfaces are held by strong adhesive forces, because the uncoated surfaces of the upper and lower plates attract water with a much greater adhesive power than the water-repellent, coated surfaces. If the complete lower surface of the upper plate is coated or if the upper plate is made from a water-repellent plastic, the drops are still held in position, but somewhat less strongly because adhesive forces only act between the lower plate and the drops. Periodically, the superimposed plates are moved towards and away from one another while maintained in parallel relation without the drops between them being torn away and without the drops being squeezed so widely that they mix together. As a result of this deformation of the drops, the substances located therein are mixed. The plates are moved by a magnet and by springs, but other means can be used for this purpose, e.g. a camshaft - spring apparatus.

The dimensions of the circular surfaces, the plate spacing and the drop diameter can be varied. Attempts at miniaturization down to 25 reaction fields per $cm^2$ have proved successful. This is made possible by the fact that the plates according to the invention cannot slide relative to one another and the maximum and minimum plate spacings are accurately maintained.

The above-described and other objects of the invention become apparent from the following description of the drawings, the description of the preferred embodiment, and the claims.

BRIEF DESCRIPTION OF THE DRAWINGS

FIG. 1 shows a base frame 1 with a stable outer frame 2 having a ledge-like bottom 3 extending around the interior thereof. At each of the four corners, the bottom 3 supports a spacer 6, which extends in one embodiment precisely 4 mm upwards. Each spacer 6 has a vertical, cylindrical recess in which is housed a telescopic spring 8. Spring 8 can be pressed in to such an extent that it no longer projects above the spacer 6. In the relaxed state, it projects preferably 3.0 to 3.5 mm above the edge of spacer 6. In a preferred construction, the base frame 1 is 128 to 8 mm long and 86 mm wide. On the inside and spaced from the bottom ledge 3, outer frame 2 is provided with an all-round slot 10 for inserting a barrier frame.

Figure 1:
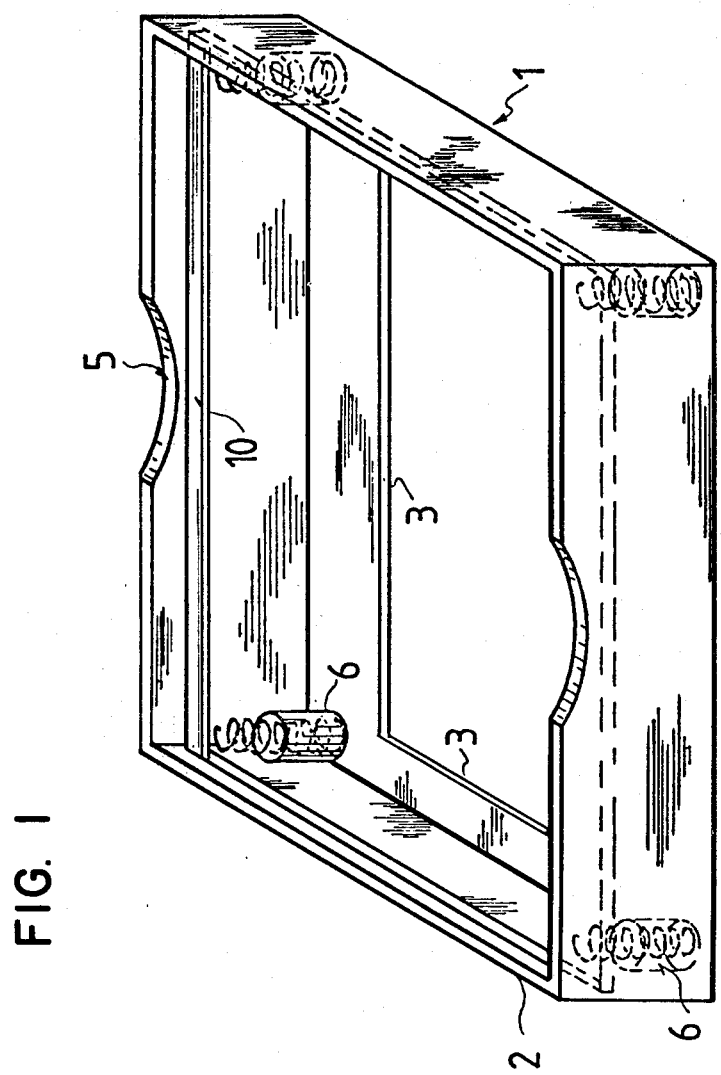
FIG. 1 is a perspective view of the upper part of a base frame.

In the centre and in the vicinity of the circular surfaces of upper and lower plates not shown in FIG. 1, the bottom of base frame 1 is open.

Figure 2:
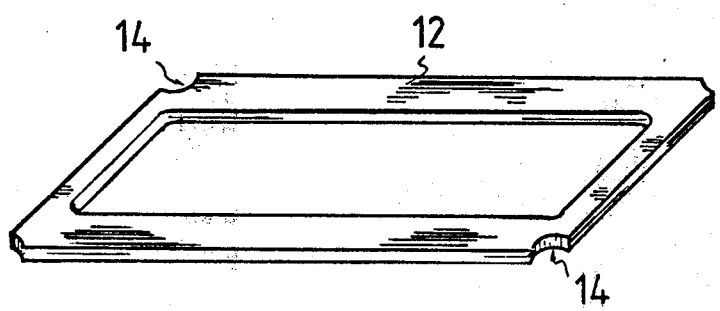
FIG. 2 is a plan view of a spacer frame for the use in the base frame according to FIG. 1.

FIG. 2 shows a spacer frame 12 which, in operation, is placed directly on bottom ledge 3. In plan view, the spacer frame 12 is approximately rectangular with a length of 118 mm and a width of 76 mm. The dimensions of the space left free inside by the spacer frame are 57×111 mm. The corners 14 of the spacer frame 12 are cut out at the positions of the spacers 6 in the form of 6×6 mm squares with internal rounded corners pointing towards the centre of spacer frame 12. The spacer frame thickness is chosen according to the particular application and further reference will be made to this hereinafter. In one construction, the spacer frame is 1 mm thick.

Figure 3:
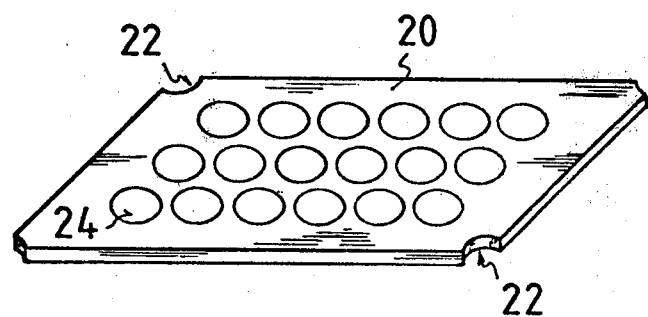
FIG. 3 is a plan view of a lower plate with uncoated circular surfaces to be placed in the base frame according to FIG. 1.

FIG. 3 is a plan view of a lower plate 20 having an approximately rectangular shape and with the preferred dimensions 118×76 mm. The corners 22 of the lower plate, as in the case of the spacer frame 12 are cut out in the vicinity of the spacers 6 shown in FIG. 1 as 6×6 mm squares with rounded inner corners. The lower plate is provided with a water repellant coating (as described below) except for a plurality of uncoated circular surfaces 24 arranged in the form of a matrix. The circular surfaces preferably have a diameter of 6 mm and a distance of 3 mm from an adjacent circular surface 24. In one embodiment, there are six lines with 12 columns of circular surfaces 24.

It is pointed out that the upper plate has an identical construction, i.e. the same dimensions and the same arrangement of circular surfaces as the lower plate 20 but no cut out corners.

Figure 4:
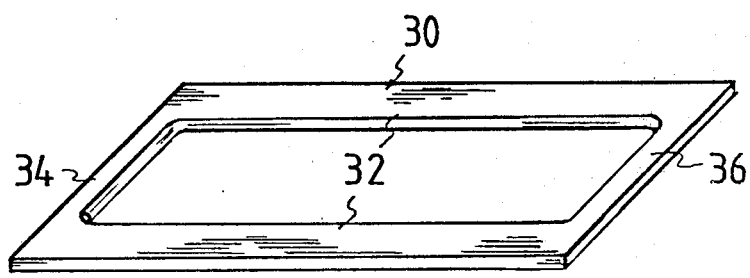
FIG. 4 is a plan view of a barrier frame to be placed in the base frame of FIG. 1.

FIG. 4 shows a rectangular barrier frame 30 with the preferred external dimensions 125.5×81 mm. Along each of its long sides, the barrier frame 30 has a 12 mm wide border 32, while borders 34 and 36 along its wide sides have different widths. In the preferred construction, the left-hand border 34 is 6 mm wide, while the right-hand border 36 is 8mm wide. This is necessary for the insertion of barrier frame 30 in base frame 1. In a preferred construction, the barrier frame is 1 mm thick.

Figure 5:
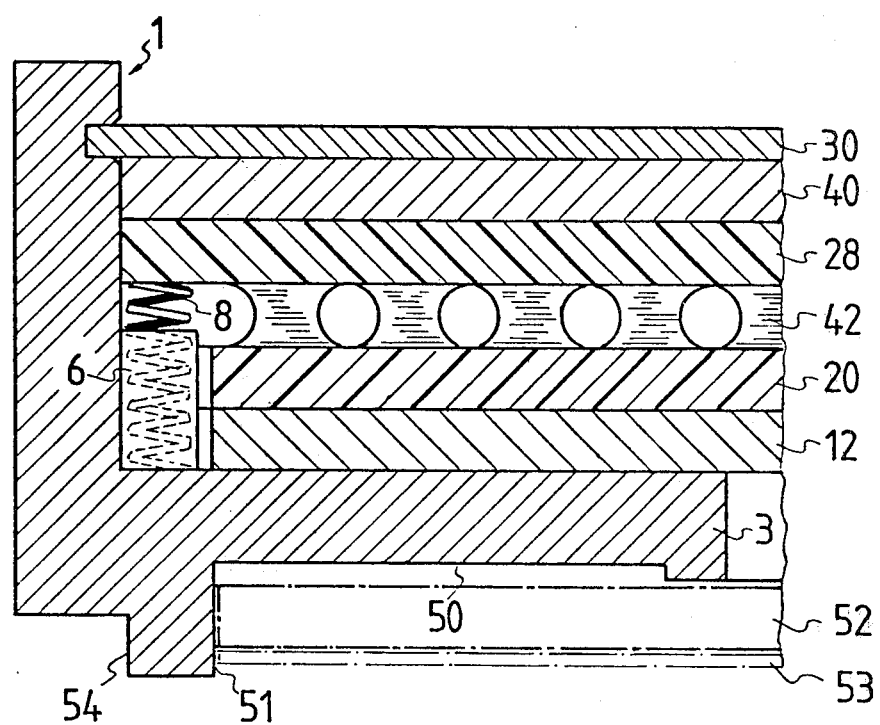
FIG. 5 is a partial section through the base frame of FIG. 1 with inserted low plate, upper plate, barrier frame and spacer frame in elevation.

FIG. 5 shows a larger scale section through base frame 1 with intimated spacers 6. A spacer frame 12, a lower plate 20, an upper plate 28, an iron plate 40 and a barrier frame 30 are placed in base frame 1. Spacer 6 is preferably 4 mm high and in the relaxed state, telescopic spring 8 projects 3.0 to 3.5 mm above it. The between 1 and 2 mm high drop layer 42 is located between lower plate 20 and upper plate 28. In the case of large drops, a thinner spacer frame is used, so that the lower plate 20 is somewhat deeper with respect to the bottom ledge 3.

As stated hereinbefore, at the corners upper plate 28 has no recesses, so that it rests on the four springs 8 of spacer 6. If it is pressed downwards counter to the action of springs 8, the drops between lower plate 20 and upper plate 28 are pressed in such a way that their width is increased. On relaxing, the upper plate 28 is pressed upwards again by springs 8, so that the drops are lifted. If upper plate 28 is removed from the base frame 1, each drop of layer 42 is divided, one part of them remaining on the circular surfaces 24 of lower plate 20, the other part adhering to the circular surfaces of upper plate 28.

According to a preferred embodiment of the invention an iron plate 40, shown in FIG. 5, is placed on upper plate 28 and when electromagnets (not shown in the drawings) are located under the base frame 1, the iron plate can be attracted intermittently at given intervals. If the electromagnet is switched off, upper plate 28 with the overlying iron plate 40 is forced upwards by springs 8. However, under the attraction of the electromagnet, iron plate 40 and upper plate 28 are moved in the direction of lower plate 20 counter to the action of springs 8. As a result, the drops are compressed.

It is obvious to the expert that the electromagnet used must have a variable pulse frequency, pulse amplitude and magnetic flux.

According to a preferred construction of the invention, the iron plate 40 is provided with holes (not shown in FIG. 5) aligned with the circular surfaces 24 of the upper and lower plates and which form the reaction fields.

So that iron plate 40 is not moved too far away from lower plate 20, the barrier frame 30 shown in FIG. 4 is introduced into slot 10 in base frame 1 (cf FIG. 1). The locking of the barrier frame 30 with respect to the base frame is brought about by two pins (not shown).

If at the end of the analysis the drops are to be pressed flat, additionally a reading frame (not shown) is placed below the barrier frame 30. Thus, e.g. in blood group determinations, the cell clots are spread out and become much clearer.

On the underside of base frame 1, shown in sectional form in FIG. 5, there is also a recess 50 with an edge 51 on which can be placed, when the frame is turned upside down, an upper plate 52 which is to undergo microscopic examination, with a superimposed glass cover 53 of the same size. Edge 51 prevents upper plate 52 and glass cover 53 from sliding relative to one another.

Edge 51 on the underside of base frame 1 has an outer shoulder 54 which fits into the inner edge of another base frame (not shown), which enables the latter to be stacked.

Another feature of the invention is that gripping channels 5 FIG. 1 are provided on the long sides of base frame 1 and do not extend completely down to the drop layer 42.

The coating of the preferably glass upper and lower plates takes place e.g. in the following manner. Firstly, upper plate 28 and lower plate 20 are carefully cleaned and degreased. Using a rubber stamp, a coating of warm, liquid grease is applied to the surfaces 24 defining the reaction fields which should remain free from the water-repellent coating. The application of the grease effects a temporary masking of the discrete plate areas which are to become the reaction fields. A solution containing e.g. polytetrafluoroethylene (TEFLON$^R$) is then sprayed over it. The grease is then washed off hot and the plates are dried and polished. As it is not easy to determine on which side the coating is located and to permit reliable identification of the specimens, the plates are marked towards the coated surface at a particularly marked point on the edges using a lacquer. If the analyses are to take place in an organic solvent, the water-repellent plates are provided with a hydrophilic coating.

If when using the apparatus according to the invention, extinction changes occur, they can be measured photometrically with the plates still superimposed.

In the case of radioimmunoassays, the radioactivity associated with one of the two plates can be measured by autoradiography thereof and subsequent densitometry of the plate density. According to another method, the reaction fields are stamped out at the end of analysis and their radioactivity is measured with a conventional counter.

If at the end of the analyses, there is to be a microscopic evaluation or measurement of the specimens on one of the two plates, said plate together with a glass cover to be placed over it are positioned in a frame in such a way that there can be no reciprocal displacement of the plate and cover.

What is claimed is:

1. An apparatus for performing microanalyses for immunological examinations, particularly blood group determinations, radioimmunoassays, enzyme immunoassays and immunofluorescent assays, as well as for non-immunological general chemical, biochemical and clinical-chemical examinations, said apparatus making it possible to examine a plurality of dissolved or dissolvable specimens at the same time, the apparatus comprising:

means for holding a plurality of superimposed plates including a lower plate and an upper plate;
   said lower plate having a plurality of reaction fields in which the reaction mixture solvent is more strongly attracted than in the area surrounding the reaction field;
   said upper plate having a solvent-repelling coating on its underside;
   means for limiting the movement of the upper plate toward the lower plate;
   means for limiting the movement of the upper plate away from the lower plate; and
   means for periodically moving the upper plate toward and away from the lower plate.

2. An apparatus according to claim 1, wherein the holding means is a substantially rectangular base frame with all-round sidewalls and an all-round bottom ledge.

3. An apparatus according to claim 1, wherein the means for limiting the movement of said upper plate toward said lower plate comprises spacers located in said means for holding a plurality of superimposed plates.

4. An apparatus according to claim 3, wherein said means for periodically moving said upper plate away from said lower plate includes compression springs located in the spacers which press the upper plate away from the lower plate.

5. An apparatus according to claim 1, wherein the means for limiting the movement of the upper plate away from the lower plate is a barrier frame inserted over the upper plate in said means for holding a plurality of superimposed plates.

6. An apparatus according to claim 5, wherein a ferromagnetic plate is placed between the barrier frame and the upper plate.

7. An apparatus according to claim 1, wherein at the same points as the lower plate, the upper plate on its underside has solvent-attracting reaction fields, whilst the areas surrounding the reaction fields are provided with a solvent-repelling coating.

8. An apparatus according to claim 3, wherein the corners of the lower plate are cut out in the vicinity of the spacers.

9. An apparatus according to claim 1, wherein said means for periodically moving said upper plate toward said lower plate comprises an electromagnet arranged below said means for holding a plurality of superimposed plates.

10. A method for the manufacture of the upper and lower plates of the apparatus according to claim 1 in which the following steps are performed:

the upper and lower plates are cleaned and degreased;
    warm, liquid grease is applied to the points of the reaction fields;
    the plates are coated with a solvent-repelling coating, preferably polytetrafluoroethylene; and
    the grease coating is washed off hot in the vicinity of the reaction fields.

11. An apparatus for performing microanalysis of a plurality of liquid specimen mixtures, said apparatus comprising a pair of superimposed plates, means for supporting said plates in spaced parallel alignment, said plates being coated with a coating repellent to the specimen mixture solvent, at least one of said plates having a plurality of discrete areas thereon which are free of said coating and are attractive to the specimen mixture solvent, said means for supporting said plates including means permitting limited relative movement of said plates toward and away from each other, and means for periodically moving said plates toward and away from each other to effect a mixing of specimens disposed on said areas.

12. The apparatus as claimed in claim 11 wherein both of said plates include discrete areas thereon which are free of said coating and attractive to the specimen mixture solvent, each area of one plate having a corresponding area on the other plate arranged in superposed alignment therewith.

13. A method of separately and simultaneously mixing a plurality of separate specimens for microanalysis comprising the steps of providing a pair of plates of similar size, establishing a plurality of discrete specimen attracting areas on at least one of said plates, placing a plurality of small drop-sized specimens on said discrete plate areas, placing said plates in closely spaced parallel relation to establish contact of said specimen drops with each of said plates, and periodically moving said plates toward and away from each other to effect a deformation of said drops and a mixing of the drop components, the movement of said plates being limited to prevent the detachment of said drops from either plate or the displacement of the drops from the discrete areas.

14. The method as claimed in claim 13 wherein said specimen attracting areas are established by providing a specimen solvent-repelling coating on the remaining surface of the plate.

15. The method as claimed in claim 13 wherein the plurality of discrete specimen attracting areas is established by the steps of:
cleaning and degreasing the plate;
temporarily masking discrete areas of said plate;
covering the plate with a specimen solvent-repelling coating; and
unmasking said discrete areas to establish specimen solvent attractive areas on said plate.

16. The method claimed in claim 15 wherein said masking step comprises the application of grease to said discrete areas.

17. The method as claimed in claim 15 wherein the coating comprises polytetrafluoroethylene.

* * * * *

UNITED STATES PATENT AND TRADEMARK OFFICE
CERTIFICATE OF CORRECTION

PATENT NO. : 4,339,241
DATED : July 13, 1982
INVENTOR(S) : Winfried A. Stocker

It is certified that error appears in the above—identified patent and that said Letters Patent is hereby corrected as shown below:

Column 1, line 48, after "slide" insert --side-slips--;

line 60, "1951" should read --1952--.

Column 3, line 53, delete -- to 8--.

Column 5, line 26 after "5" delete --FIG.1--.

Signed and Sealed this

Twelfth Day of October 1982

[SEAL]

Attest:

GERALD J. MOSSINGHOFF

Attesting Officer   Commissioner of Patents and Trademarks